United States Patent [19]

Contestable et al.

[11] Patent Number: 5,589,344
[45] Date of Patent: Dec. 31, 1996

[54] TEST KIT AND METHOD FOR COMPETITIVE SPECIFIC BINDING ASSAY

[75] Inventors: Paul B. Contestable; Brian A. Snyder, both of Rochester, N.Y.

[73] Assignee: Johnson & Johnson Clinical Diagnostics, Inc., Rochester, N.Y.

[21] Appl. No.: 259,942

[22] Filed: Jun. 15, 1994

[51] Int. Cl.$^6$ .................. G01N 33/53; G01N 33/543
[52] U.S. Cl. .................. 435/7.9; 435/7.93; 436/518
[58] Field of Search .................. 435/7.9, 7.93, 435/7.94, 810, 964, 971, 973, 975; 436/536, 538, 540, 544, 518

[56] References Cited

U.S. PATENT DOCUMENTS

| | | | |
|---|---|---|---|
| 3,850,752 | 11/1974 | Schuurs et al. | 435/7.93 |
| 4,218,436 | 8/1980 | Fitzpatrick | 530/389.2 |
| 4,859,583 | 8/1989 | Heller et al. | 435/7.7 |
| 5,089,391 | 2/1992 | Buechler et al. | 435/7.1 |
| 5,234,812 | 8/1993 | Buck et al. | 435/7.5 |

FOREIGN PATENT DOCUMENTS

| | | |
|---|---|---|
| 0147848 | 12/1984 | European Pat. Off. |
| 166583 | 1/1986 | European Pat. Off. |
| 336647 | 10/1989 | European Pat. Off. |
| 0517327 | 6/1992 | European Pat. Off. |
| 53-230 | 2/1989 | Hungary |

OTHER PUBLICATIONS

Chemical Abstracts, vo. 110, No. 9, Feb. 7, 1989; B. Orsini et al. "A second antibody solid–phase enzyme immunoassay of prostaglandin E2 in human gastric juice" p. 66, No. 69 502x; & Clin. Chim. Acta 1988 178(3), 305–12, Abstract only.

Chemical Abstracts, Vo. 103, No. 15, Oct. 14, 1985; T. Tanaka et al. "Rat monoclonal antibody specific for prostaglandin E structure", p. 24, No. 116424r; & Biochem. Biophys. Acta 1985, 836(1), 125–33, Abstract only.

*Primary Examiner*—Mary E. Mosher
*Assistant Examiner*—Donna C. Wortman

[57] ABSTRACT

One or more specific binding ligands can be detected with a competitive immunoassay which utilizes a water-soluble conjugate of ligand and reporter enzyme for each target ligand. Target ligand is allowed to compete for a first receptor with the conjugate. Uncomplexed conjugate is then contacted with an immobilized second receptor to form a reaction product which can be used to generate a detectable signal. This assay provides a direct correlation of the generated signal to the one or more target ligands.

14 Claims, 2 Drawing Sheets

TEST KIT AND METHOD FOR COMPETITIVE SPECIFIC BINDING ASSAY

FIELD OF THE INVENTION

This invention relates to a rapid specific binding assay for a target ligand using a competitive binding assay format. The invention also relates to test kits useful in carrying out the assay. One utility of the invention is in diagnostics to detect various specific binding ligands which can be indicators of disease.

BACKGROUND OF THE INVENTION

There is a continuing need in medical practice and research, and in analytical and diagnostic procedures, for rapid and accurate determinations of chemical and biological substances present in various fluids, such as biological fluids. For example, the presence of drugs, narcotics, hormones, proteins, toxins, microorganisms, viruses, steroids or nucleic acids must be rapidly and accurately detected for effective research, diagnosis or treatment of various diseases or conditions.

Prostaglandin $E_2$ ($PGE_2$) is a potent biochemical mediator of inflammation in the body. Elevated levels of $PGE_2$ in crevicular fluid have been shown to be an indicator of periodontal disease. Due to the cyclical nature of periodontal diseases, an accurate measure of disease activity would be useful to determine periods of disease exacerbation and to aid in favorable disease treatment. If $PGE_2$ can be detected at very low concentrations (100 nmolar or less), the clinical usefulness of $PGE_2$ as an indicator of periodontal disease is optimized.

A wide variety of analytical methods have been developed in recent decades to detect various chemical or biological substances. Most of such methods rely on what are known in the art as "specific binding" reactions in which an unknown substance to be detected (known as a "specific binding ligand") reacts specifically and preferentially with a corresponding "receptor" molecule. Most well known specific binding reactions occur between immunoreactants, such as antibodies and antigens (foreign substances which produce immunological responses), but other specific binding reactions (such as avidin with biotin or a sugar with a lectin) are also known.

Many of the assay formats known in the art require one or more of the reactants to be immobilized on a solid substrate so that nonimmobilized reactants can be separated from immobilized reactants. "Sandwich" and "direct binding assays" are some of the assay formats which have been used in the art which require separation steps.

The standard immunological techniques, however, are more difficult to use with success in the detection of low molecular weight target specific binding ligands, such as $PGE_2$. It is particularly desirable to detect low concentrations (1 nmolar or less) of such ligands, but the standard immunological techniques are not always dependable for this purpose.

Quantification of low molecular weight target specific binding ligands generally involves a competition between unlabeled ligand (in a test sample) and labeled ligand for the binding sites of a receptor for the ligand. This is a typical competitive specific binding assay. Ligand in the test sample displaces labeled ligand from the receptor, and the amount of displacement is quantified by various methods. Measurement of bound labeled ligand results in an inverse correlation between the amount of ligand in the sample and the generated signal. Measurement of unbound labeled ligand will yield a positive correlation.

Generally, the signal from bound ligand is easier to measure, but the signal is more difficult to interpret by health practitioners where there is a lack of sophisticated diagnostic training and equipment (for example, in doctors' offices).

Another problem with standard competitive specific binding assays is that the measurement of the free or bound labeled ligand is limited by the efficiency of the separation of free and bound molecules. If the free labeled ligand is not successfully separated from the bound labeled ligand, the sensitivity and specificity of the assay will be adversely affected.

Thus, there is a need for a sensitive competitive binding assay in which efficient separation and measurement of free labeled ligand is achieved to rapidly and easily detect low concentrations of various target specific binding ligands (especially those of low molecular weight).

Copending and commonly assigned U.S. Ser. No. 08/250,980, entitled "Specific Binding Assay and Test Kit Using Enzyme Inhibitor and Anti-Inhibitor Antibodies" and filed on May 31, 1994 by Contestable, Snyder, Corona-Howard and Grogan, provides such an assay which solves the noted problems.

However, the assay of that application requires the use of some sophisticated antibodies which are specific to the reporter enzyme used to generate signal. Those antibodies have other critical properties which render the assay advantageous. Such reagents may be difficult to develop or manufacture consistently for certain assays, and it would therefore be desirable to avoid their use if possible while retaining the remarkable advantages provided by the general assay format. Thus, an alternative assay which uses less sophisticated reagents and which is simpler to manufacture and to use is desired.

U.S. Pat. No. 4,859,583 (Heller et al) describes a chemiluminescent immunoassay for low molecular weight antigens using a device having multiple chambers. In the described assay, sample antigen displaces labeled antigen bound to antibody. The labeled antigen diffuses into a second chamber wherein a light signal is generated. There are several problems associated with this approach, but the primary problem is that the assay is necessarily slow since diffusion must occur across a membrane. Moreover, the device is complicated and requires a suitable membrane for each given analyte (antigen). It would be desirable to have a faster and simpler assay for low molecular weight analytes.

SUMMARY OF THE INVENTION

The problems noted above are solved with a specific binding method for the detection of a target specific binding ligand comprising the steps of:
A) bringing together, in any order:
  1) a fluid sample suspected of containing a target specific binding ligand,
  2) a first receptor for the target specific binding ligand, and
  3) a water-soluble conjugate of the target specific binding ligand and a reporter enzyme,
to form a mixture containing a complex between the first receptor and either the target specific binding ligand or the water-soluble conjugate,
B) bringing together a sample of the mixture containing any uncomplexed water-soluble conjugate, and an immobilized second receptor, the second receptor being specific for either the reporter enzyme or the target specific binding ligand, to form a water-insoluble reaction product of the immobilized second receptor and any uncomplexed water-soluble conjugate, provided that when the first receptor is water-soluble, the immobilized second receptor is specific for the target specific binding ligand, C) separating the water-insoluble reaction product formed in step B) from any unreacted water-soluble conjugate, and D) detecting any signal generated from the separated water-insoluble reaction product as a determination of the target specific binding ligand in the fluid sample.

This invention also provides a test kit useful for the detection of a target specific binding ligand comprising, in individual packaging:

a water-soluble conjugate of a target specific binding ligand and a reporter enzyme, a first receptor for the target specific binding ligand, and an immobilized second receptor, the second receptor being specific for either the reporter enzyme or the target specific binding ligand, provided that when the first receptor is water-soluble, the immobilized second receptor is specific for the target specific binding ligand.

The present invention is a specific binding assay in which the signal from the activity of the reporter enzyme is directly proportional to the amount of target specific binding ligand in the assay system. It provides for the rapid and easy detection of low concentrations of target specific binding ligands, especially low molecular weight ligand such as $PGE_2$. Thus, the assay can be used to advantage in the diagnosis or treatment of periodontal diseases.

In one embodiment, the assay of this invention uses a quick competitive separation of free and bound reporter enzyme labeled ligand using an immobilized first receptor. Free labeled ligand is then complexed with immobilized second receptor molecules specific for either the ligand or the reporter enzyme, and the resulting reaction product is typically captured in a disposable test device for easy signal generation and detection. In a preferred embodiment, use of distinct immobilized receptors and water-soluble conjugates for each target ligand allows for the detection and differentiation of multiple target ligands in a single test device.

In another embodiment, the first receptor is water-soluble (non-immobilized), and the immobilized second receptor is reacted with ligand conjugated to reporter enzyme in order to detect the presence of ligand in the sample.

DETAILED DESCRIPTION OF THE INVENTION

Definitions:

The present invention can be used to qualitatively, quantitatively or semi-quantitatively detect one or more of a wide variety of target specific binding ligands (identified as ligands hereinafter) for which receptor molecules are available or manufacturable. Examples of ligand-receptor complexes (that is, a reaction product of ligand and corresponding receptor) include, but are not limited to, antibody-antigen, antibody-hapten, avidin-biotin, sugar-lectin, gelatin-fibronectin and Protein A-IgG complexes. For the purposes of this invention, complementary nucleic acids (that is, hybridized products of complementary strands) are also considered ligand-receptor complexes. Such complementary nucleic acids need not be complementary at every base pair. One strand can be longer than the other, or one strand can have a plurality of shorter complementary strands.

Ligands include, but are not limited to, peptides, polypeptides, proteins (including enzymes, antibodies, antigenic proteins, glycoproteins, lipoproteins and avidin), hormones (such as thyroxine, triiodothyronine, human chorionic gonadotropin, estrogen, ACTH and substance P), immune system modulators (such as interleukin-1, interleukin-6 and tumor necrosis factor $\alpha$), vitamins, steroids, carbohydrates (such as polysaccharides), glycolipids, drugs (such as digoxin, phenytoin, phenobarbital, morphine, carbamazepine and theophylline), antibiotics (such as gentimicin), components of cells and viruses (such as Streptococcal species, herpes viruses, Gonococcal species, Chlamydial species, retroviruses, influenza viruses, Prevotella species, Porphyromonas species, Actinobacillus species and Mycobacterium species), nucleic acids (including single- and double-stranded oligonucleotides), pharmaceuticals, haptens, lectins, biotin, and other materials readily apparent to one skilled in the art. In preferred embodiments, the ligands are antigenic substances (such as the drugs noted above) or antibodies (including anti-antibodies).

This invention is particularly useful for the detection of low molecular weight target specific binding ligands. By "low molecular weight target specific binding ligands" is meant compounds having a molecular weight of less than 500 daltons and which are capable of complexing with only a single corresponding receptor molecule (either because of only a single epitopic binding site, or because of steric hindrances). Such ligands include, but are not limited to, $PGE_2$ and other arachidonic acid metabolites, digoxin, diphenylhydantoin, carbamazepine, phenobarbital and other materials which would be readily apparent in the art. In a most preferred embodiment, this invention is useful for the efficient and rapid detection of $PGE_2$.

As used herein (unless otherwise noted), the term "antibody" includes whole immunoglobulin molecules having a single specificity as is conventional in the art. In addition, the term is intended to include chemically prepared fragments [such as Fab, F(ab)', F(ab)$_2$ fragments] of such molecules and genetically prepared equivalents thereof (such as "single chain antibody fragments" or ScFv fragments). Each type of antibodies described herein can be monoclonal or polyclonal.

Monoclonal antibodies include those molecules generally prepared using conventional hybridoma technology, but they can also be prepared by electrofusion, viral transformation and other procedures known in the art.

Generally, the monoclonal antibodies used in the invention are prepared by immunizing a suitable mammal (such as a mouse or rat) with the appropriate antigen, such as a reporter enzyme (or the antigen conjugated to carrier proteins), following the conventional procedures described by Kohler et al, *Nature* 256, 495 (1975).

A population of splenocytes from the immunized animals can be fused with suitable hybridoma cell lines in the presence of polyethylene glycol (PEG1450) or another fusogen following the teaching of Lane [*J. Immunol. Methods* 81, pages 223–228 (1985)]. The resulting hybridized cells are diluted into selective media, distributed into microtiter plates and cultured for 7 to 21 days before screening to see what type of properties the antibodies possess. A specific procedure for preparing the certain useful antibodies is illustrated below.

A variety of myeloma cell lines are commercially available for hybridization with the mammal spleen cells. Sources of such cell lines include the American Type Culture Collection (ATCC) in Rockville, Md. Particularly useful myeloma cell lines include Sp2/0-Ag14 and P3x63Ag8 myeloma cells, both available from the ATCC. The first cell line is preferred.

In the preparation of monoclonal antibodies for use in this invention, selected hybridomas were cloned in soft agar and individual clones were plucked, cultured using conventional means and screened using the procedures described above. Monoclonal antibodies were grown in shaker flasks, and the antibodies collected and purified using conventional affinity chromatography on either immobilized Protein A or Protein G. Other conventional purification procedures can be used if desired.

Assay Protocol:

In general, the assay protocol of this invention comprises bringing together the following reagents in any order:

1) the ligand (such as an antigenic substance) in a fluid sample of some type,
2) a first receptor (such as an antibody) which is specific to and reactive with the ligand (which can be conjugated to reporter enzyme, or in free form) in the fluid sample, and
3) a water-soluble conjugate of the target ligand and a reporter enzyme.

Once these reagents are brought together, appropriate reactions occur. Specifically, the target ligand and water-soluble conjugate compete for available sites on the first receptor, thereby forming specific binding complexes.

If the first receptor is immobilized in some fashion, the water-insoluble specific binding complex thus formed is then separated from uncomplexed water-soluble conjugate in a resulting supernatant. Separation means are described in more detail below.

Once separation is accomplished, a sample of the supernatant containing any uncomplexed water-soluble conjugate is brought together with an immobilized second receptor. This second receptor is specific for either the reporter enzyme of the conjugate, or the ligand portion of the conjugate.

The result of this contact is the formation of a water-insoluble reaction product of conjugate with immobilized second receptor. This reaction product is then separated from any remaining unreacted water-soluble conjugate. Signal is generated from the presence of the active reporter enzyme in the immobilized reaction product in direct proportion to the amount of ligand in the fluid sample using appropriate signal generating reagents (described below).

Thus, if no ligand is present in the original fluid sample, there will be no water-soluble conjugate present in the supernatant after the first separation step. When no water-soluble conjugate is present in the supernatant, no conjugate reacts with the immobilized second receptor, and no signal is generated. When ligand is present in the fluid sample, water-soluble conjugate will be present in the supernatant. This conjugate complexes with the immobilized second receptor, thereby providing detectable immobilized reaction product in direct proportion to the amount of ligand in the fluid sample.

If the first receptor is water-soluble (not immobilized), the reaction solution containing a mixture of complexed and uncomplexed materials is contacted directly with the immobilized second receptor which is specific to the target specific binding ligand only. Any complexes of first receptor with the conjugate of ligand and reporter enzyme, are washed away as they cannot react with the immobilized second receptor. Hence, no prior separation of complexed and uncomplexed materials using the first receptor is required. Signal generation and detection is achieved in a similar fashion as described above.

In the various steps described above, the reagents noted above can be brought together at suitable temperature, generally in the range of from about 10° to about 35° C., and preferably at room temperature. The time for mixing can vary from a few seconds to 120 minutes, although typically the mixing step requires less than about five minutes. It is also preferred that the entire method be carried out within about 20 minutes.

The ligand to be detected may be present in any of a wide variety of fluid samples (or aqueous solutions) of animal or human body fluids, tissues or waste products including, but not limited to, whole blood, serum, plasma, lymph fluid, bile, urine, spinal fluid, lacrimal fluid, swab specimens, stool specimens, semen, vaginal secretions, saliva, crevicular fluid, and others readily apparent to one skilled in the art. The size of the fluid sample can vary widely as is known in the art, but typically it is at least about 1–10 µl.

First and second receptor molecules are made available for reaction with the ligand or the reporter enzyme label attached to the ligand. Generally, such receptors are antibodies specific to the ligand or to the reporter enzyme (described below).

In one embodiment, both first and second receptors are provided in immobilized form on the same or different water-insoluble supports. Suitable supports include, but are not limited to, polymeric, magnetic or glass particles, polymeric or glass filtration membranes, cellulosic filter papers, polymeric films, glass slides, test tubes, magnetic ferrofluids, test wells of test devices or microtiter plates or other materials readily apparent to one skilled in the art. Preferably, the receptors are immobilized on the same or different polymeric particles designed for this purpose, which particles are well known in the art. Reactive groups on the surface of particles include, but are not limited to, carboxy, 2-substituted ethylsulfonyl, vinylsulfonyl, epoxy, aldehyde, active halo atoms, amino, hydrazine and active esters such as succinimidoxycarbonyl.

Particularly useful particulate supports are described, for example in EP-A-0 323 692 (published Jul. 12, 1989) and U.S. Pat. No. 4,997,772 (Sutton et al, incorporated herein by reference) which are prepared from one or more ethylenically unsaturated polymerizable monomers having active halo atoms, activated 2-substituted ethylsulfonyl or vinylsulfonyl groups. Useful carboxy-containing polymeric particles are described in U.S. Pat. No. 5,262,297 (Sutton et al), incorporated herein by reference. Other carboxy-containing polymeric particles are described in the art and many are commercially available.

Attachment of the receptor to the support can be accomplished using any of a variety of conventional procedures, such as coating to adsorb the receptor molecules or incubating to allow covalent reaction with reactive groups on the support. Such procedures are described, for example, in U.S. Pat. No. 5,252,457 (Snodgrass et al) and U.S. Pat. No.

5,262,297 (Sutton et al), both incorporated herein by reference. Alternatively, the receptor can be attached to supports, such as polymeric particles, having linking groups attached thereto, and such linking groups can be chemical moieties extending from the support or biological linking moieties such as peptides or antibodies to which the receptor can be complexed.

The amount of first receptor used in the method of this invention is generally from about $10^{-11}$ to about $10^{-7}$ molar, with from about $10^{-9}$ to about $10^{-8}$ being preferred.

The water-soluble conjugates of ligand and reporter enzyme used in the practice of this invention can be prepared using any conventional technique of the art for covalently binding proteins, hormones, drugs or other chemical or biological compounds having requisite reactive groups. Thus, the various reactive groups of the ligand and reporter enzyme can be considered in choosing the means for making the conjugate, such groups including, but not limited to, carboxy, amino, hydroxy, thiol and imidazole groups. Useful methods of binding include, but are not limited to, binding of peptides, periodate oxidation, use of glutaraldehyde, dication ethers, carbamoylonium salts, carbodiimides or N-hydroxysuccinide, and others readily apparent to one skilled in the art. Details for each of these and other methods are found in voluminous literature, including Williams et al *Method in Immunology and Immunochemistry*, Academic Press, New York, 1976, and Yoshitake et al, *Eur. J. Biochem.* 101, 395 (1979).

The amount of water-soluble conjugate used in the first step of the method is generally sufficient to provide at least about $10^{-11}$ molar reporter enzyme so that background is negligible and kinetics for complex formation are acceptable. In addition, the amount is generally less than or equal to about $3 \times 10^{-8}$ molar so that enzyme substrates for producing signal are not reacted too quickly.

Reporter enzymes useful in this invention as part of the water-soluble conjugate are enzymes which are typically used as labels in diagnostic methods. They include, but are not limited to, a peroxidase, glucose oxidase, β-galactosidase, urease, alkaline phosphatase, creatine kinase, uricase, glucose-6-phosphate dehydrogenase and others readily apparent to one skilled in the art. A peroxidase (from any of various sources) is preferred, and horseradish peroxidase is most preferred.

The second receptor used in step B) of the practice of this invention can be the same as or different from the first receptor used in step A) of the method. That is, it can be a receptor, such as an antibody, for the ligand. Antibodies for various ligands are generally well known in the art, either by purchase from commercial sources or prepared using known techniques for preparing polyclonal or monoclonal antibodies. In the embodiments described below where multiple ligands are detected simultaneously, second receptors are used which are specific for the ligands to be detected.

Alternatively, the second receptor can be an antibody specific for the reporter enzyme of the water-soluble conjugate, which antibody does not significantly inhibit enzymatic activity. That is, the antibodies inhibit enzymatic activity by no more than 20% or less (and preferably by 6% or less). Such antibodies can be prepared using conventional methods described above, followed by a screening process to find antibodies having the desired properties. They are identified herein as "binder" antibodies. For example, screening for binder antibodies specific for horseradish peroxidase is described below as an illustration of how such screening can be carried out for a given reporter enzyme, but this invention is not to be construed as limited to the use of this reporter enzyme only. It is believed that antibodies to other reporter enzymes could be similarly prepared and identified using the teaching provided herein. Screening for specificity to the reporter enzyme can be readily accomplished using conventional Enzyme Linked Immunosorbent Assays (ELISA) in polystyrene microtiter plates containing adsorbed horseradish peroxidase conjugate.

Specificity for Horseradish Peroxidase

A sample (50 μl/plate well) of each hybridoma culture supernate is placed in a microtiter well coated with a conjugate of horseradish peroxidase and an irrelevant antibody (an antibody not reactive in the system) obtained, for example, from Jackson Immunoresearch. After a 30–60 minute incubation, the plates are washed with a suitable buffered solution of a nonionic surfactant, and the presence of mouse or rat horseradish peroxidase specific monoclonal antibodies is detected with a conjugate of anti-mouse IgG or anti-rat IgG and alkaline phosphatase (conjugate with anti-mouse Fc obtained from, for example, Jackson Immunoresearch). A dye signal can be generated by adding the substrate o-nitrophenyl phosphate disodium salt (4 mg/ml) in tris(hydroxymethyl)aminomethane buffer (1.5 molar, pH 8). Other signal producing reagents, or enzyme labels can be similarly used. The antibodies which provide a dye signal after about 30 minutes of at least twice as dense as a background signal are considered to be specific for horseradish peroxidase. The dye signal can be measured using a conventional spectrophotometer.

Binder antibodies specific to horseradish peroxidase can be screened for inhibitory function in the following manner. As noted above, it is desired that the binder antibodies exhibit little or no inhibition of the enzymatic activity.

Assay for Enzyme Inhibition:

A sample (50 μl) of each culture supernate is placed in a microtiter plate well, followed by addition of a solution (50 μl) of horseradish peroxidase (0.2 nmolar), gelatin (0.8%) in phosphate buffered saline, and the resulting mixtures are allowed to stand for 10 minutes at room temperature. Residual enzyme activity is then determined by adding 100 μl of the horseradish peroxidase substrate, o-phenylenediamine (1 mg/ml) in citrate/phosphate buffer (50 mmolar, pH 5.5, 1:1 mix ratio), and measuring the amount of dye signal at 450 nm using a conventional spectrophotometer (rate of 100 mOD/minute). Other substrates, or dye providing reagents can be similarly used.

Those culture supernates that inhibit horseradish peroxidase by less than 20% (compared to a control without the presence of monoclonal antibody) are considered for use as binder antibodies. Preferably these antibodies diminish the activity of the reporter enzyme (such as horseradish peroxidase) by no more than 6%.

The dissociation constants ($K_d$) for binder antibodies are generally less than or equal to 50 nmolar, preferably less than or equal to 25 nmolar and more preferably less than or equal to 5 nmolar. It should be understood that the $K_d$ values noted herein are relative measures for the antibodies, and that various conventional methods for measuring that parameter may give slightly lower or higher values. Most of the $K_d$ values reported in Table I below (except for "B5-10") were determined by measuring the concentration of binder antibody required to prevent 50% inhibition of 0.1 nmolar of the reporter enzyme (such as horseradish peroxidase) by 10 nmolar of a monoclonal antibody identified as "4–22.2" which was determined by the screening test identified above to inhibit about 99% of the enzymatic activity. Monoclonal antibody 4–22.2 was prepared using the hybridoma cell line HB 11603 which has been deposited with the ATCC. The $K_d$ of binder antibody B5-10 was measured by a conventional competitive assay measuring the amount of bound and unbound antibody in the presence of horseradish peroxidase.

The following Table I lists useful binder monoclonal antibodies specific to horseradish peroxidase useful in the practice of this invention by species, isotype, $K_d$ and maximum horseradish peroxidase inhibition:

TABLE I

| Antibody | Species/ Isotype | Kd (nmolar) | Max. Inhibition (%) |
|---|---|---|---|
| 6-89.1 | rat*/IgG2a | 3.5 | 6 |
| 6-82.1 | rat*/IgG2a | 7.0 | 10 |
| 6-71.2 | rat*/IgG2a | 10 | 8 |
| 6-55.2 | rat*/IgG1 | 20 | 6 |
| B5-10 | mouse**/IgG1 | 10 | 1 |
| 7-32.2 | mouse**/IgG2a | 3.3 | 0 |

*Sprague-Dawley rats
**CAF$_1$ mice

The 6-89.1 and 7-32.2 monoclonal antibodies are representative binder antibodies for horseradish peroxidase. They were prepared using the novel hybridoma cell lines identified herein as HB 11635 and HB 11604, respectively, which have been deposited with the ATCC.

Signal generated by the reporter enzyme in the course of the assay of this invention can be a chemiluminescent, electrochemical or colorimetric signal depending upon the particular reporter enzyme and corresponding reagents (such as substrates) used to generate the signal.

Chemiluminescent signals can be generated in a wide variety of ways in response to a reporter enzyme. In most chemiluminescent systems, the reporter enzyme is a peroxidase, and an oxidant such as hydrogen peroxide is present or generated in some fashion (for example, the reaction of an oxidase with its substrate). Useful chemiluminescent signals are generated using, for example, acridinium salts, dioxetanes, tetrakis(dimethylamino)ethylene, luciferin, lucigenin, oxalyl chloride, certain oxidases (for example, xanthine oxidase) and 2,3-dihydro-1,4-phthalazinediones (such as luminol and isoluminol). Many examples of such compounds and their uses are known in the art, for example, in U.S. Pat. No. 4,383,031 (Boguslaski et al), U.S. Pat. No. 4,598,044 (Kricka et al), U.S. Pat. No. 4,729,950 (Kricka et al), U.S. Pat. No. 5,108,893 (Baret) and *Chemiluminescence in Organic Chemistry* (Gundermann et al, Springer-Verlag, Berlin, 1987, pages 204–207). Where a chemiluminescent signal is generated, preferably peroxidase is used as the reporter enzyme, and luminol or a similar compound is used as a signal generating reagent.

Preferably, a colorimetric signal is generated in the method of this invention. Such signals can be achieved using a wide variety of reporter enzymes and reagents, as is well known in the art. Where the reporter enzyme is a peroxidase, as is preferred, useful dye-providing reagents include, but are not limited to, tetramethylbenzidine and derivatives thereof, o-phenylenediamine, triarylmethanes, and imidazole leuco dyes, such as the triarylimidazole leuco dyes described in U.S. Pat. No. 4,087,747 (Bruschi) and U.S. Pat. No. 5,024,935 (McClune), both incorporated herein by reference. Substrate solutions for the various reporter enzymes are provided in a wash solution or at the end of the assay. One useful substrate solution for the triarylimidazole leuco dyes includes hydrogen peroxide, and an electron transfer agent such as 4'-hydroxyacetanilide or 3'-chloro-4'-hydroxyacetanilide in a suitable buffer.

The amount of various reagents needed to produce a desired signal would be readily apparent to one skilled in the art from consulting the voluminous literature available for the various signal producing systems. Specific enablement for a preferred colorimetric system is shown below in the examples.

The equipment needed for detecting the desired signal generated in the assay also would be readily apparent to one skilled in the art. Some colorimetric signals could be readily evaluated from the user's visual observations, but more generally, the signals are evaluated using appropriate apparatus for receiving and evaluating colorimetric, fluorimetric or chemiluminescent signals.

When the first receptor is immobilized, between steps A) and B), an intermediate separation step is carried out. The water-insoluble complex formed between immobilized first receptor and either the ligand or water-soluble conjugate is separated from uncomplexed materials (including uncomplexed water-soluble conjugate) using any suitable equipment and procedure. For example, the reaction mixture from step A) can be filtered using any of a variety of filter materials which will let supernatant (containing water-soluble materials) pass through while retaining the water-insoluble complex. Alternatively, the supernatant can be decanted from the water-insoluble complex which may be attached to a microtiter plate, test tube or other container device. Preferably, the water-insoluble complex is attached to particles of a suitable material (such as polymeric particles as described above), and such particles are readily filtered or centrifuged.

Useful filtration devices would be readily apparent to one skilled in the art. Preferred filtration devices are described in U.S. Pat. No. 4,948,561 (Hinckley et al, FIG. 1).

A most preferred filtration device contains a microporous filtration membrane having an average pore size of from about 0.5 to about 10 μm. Such membranes are commercially available as LOPRODYNE™ membranes from Pall Corp.

Step B) and the following steps in the method of this invention can be carried out in a suitable container wherein immobilized second receptor and the initial reaction solution can be suitably mixed. For example, this mixing can be carried out in microtiter plates, test tubes, microfuge tubes and other devices readily apparent to one skilled in the art. Preferably, the method is carried out in disposable test devices in which the second receptor is immobilized in a suitable fashion. Such test devices would be readily apparent to one skilled in the art and would include such devices as are described in U.S. Pat. No. 3,825,410 (Bagshawe), U.S. Pat. No. 3,888,629 (Bagshawe), U.S. Pat. No. 3,970,429 (Updike), U.S. Pat. No. 4,446,232 (Liotta), U.S. Pat. No. 4,833,087 (Hinckley), U.S. Pat. No. 4,877,586 (Devaney, Jr. et al), U.S. Pat. No. 4,921,677 (Hinckley et al), U.S. Pat. No. 4,923,680 (Nelson), U.S. Pat. No. 4,948,561 (Hinckley et al), U.S. Pat. No. 4,988,627 (Smith-Lewis) and U.S. Pat. No. 5,132,085 (Pelanek). Most preferred test devices contain multiple test wells containing microporous filtration membranes (such as LOPRODYNE™ or BIODYNE™ membranes from Pall Corp.). Such devices are available from Eastman Kodak Company in SURECELL™ or EVAL-USITE™ test kits. The immobilized second receptor, if desired, can be disposed on the membranes prior to use in the method of this invention.

The separation step C) of the claimed method can be carried out in any desirable fashion. The procedure and equipment described above for the intermediate separation step can be used in step C). Preferably, the water-soluble reaction product is separated from unreacted water-soluble conjugate in the same disposable test device as described above. Any signal generated from the separated reaction product can also be detected in the disposable test device in such instances.

In one preferred embodiment, two or more different ligands can be detected simultaneously using the same filtration and test devices. Such a specific binding method for the detection of a two or more target specific binding ligands comprises the steps of:

A) bringing together, in any order:
1) a fluid sample suspected of containing two or more target specific binding ligands,
2) an immobilized first receptor for each of the target specific binding ligands, and
3) two or more water-soluble conjugates, there being a conjugate formed from each target specific binding ligand and the same reporter enzyme, to form two or more distinct water-insoluble complexes between the immobilized first receptors and either the corresponding target specific binding ligands or water-soluble conjugates, B) separating the water-insoluble complexes formed in step A) from a supernatant containing any uncomplexed water-soluble conjugates, C) bringing together a sample of the supernatant containing any uncomplexed water-soluble conjugates, and an immobilized second receptor for each of the target specific binding ligands, the immobilized second receptors being disposed in distinct regions of a water-insoluble support, to form water-insoluble reaction products of the immobilized second receptors and any uncomplexed water-soluble conjugates in the respective distinct regions on the water insoluble support, D) separating the water-insoluble reaction products formed in step C) from any unreacted water-soluble conjugates, and E) detecting any signals generated from the separated water-insoluble reaction products in the distinct regions on the water-insoluble support as a determination of the two or more target specific binding ligands in the fluid sample.

Useful water-insoluble supports for detecting multiple ligands in the noted method can be films, papers, membranes or any other water-insoluble material which is inert to the reagents in the assay and on which distinct deposits of immobilized second receptors can be disposed. Such deposits can be disposed in any desired configuration, including dots, stripes and symbols (see for example, U.S. Pat. No. 5,132,085 and EP-A-0 439,210). Preferably, the deposits of immobilized second receptors are disposed as distinct particulate dots on a microporous membrane in a single test device.

The reagents and devices described herein and used in the practice of the method of this invention can be supplied as individually packaged components of a test kit. Such kits contain a water-soluble conjugate of a target specific binding ligand and a reporter enzyme, a first receptor (immobilized or not) as described above, and an immobilized second receptor as described above. In most embodiments, the test kits include all of these reagents as well as suitable reagents for providing a colorimetric, fluorometric or chemiluminescent signal in response to the reporter enzyme, wash solutions, disposable test devices, filtration devices, and instructions for carrying out the method of the invention. The kits can also include the individual components needed to detect more than one target specific binding ligand, that is including multiple first receptors, second receptors and other reagents as one skilled in the art would understand.

The following examples are illustrative of the invention and not meant to be limiting. All percentages are by weight, unless otherwise indicated.

Materials and Methods for Examples:

Preparation of Receptor Monoclonal Antibody Specific to Horseradish Peroxidase:

A representative monoclonal binder antibody identified above as 6–89.1 in Table I was prepared as follows:

Sprague-Dawley rats were injected with a solution of horseradish peroxidase (400 µg) in commercially available TDM/MPL emulsion adjuvant (RIBI Corporation) four times at four week intervals. A fifth injection was made with horseradish peroxidase (400 µg) in phosphate buffered saline solution. Three days later, splenocytes from the immunized rats were fused with cells from the Sp2/0-Ag14 myeloma cell line using conventional procedures.

Screening of the resulting antibodies for specificity to horseradish peroxidase was carried out as described above by adding 50 µl of the culture supernatant to the wells of a microtiter plate coated with a conjugate of horseradish peroxidase and anti-mouse antibody. The bound antibody was detected by adding a conjugate of alkaline phosphatase with goat anti-mouse IgG Fc (Jackson Immunoresearch), following by signal generation using 4 mg/ml p-nitrophenyl phosphate disodium salt (Sigma Chemical) as substrate for the alkaline phosphatase in tris(hydroxymethyl)aminomethane buffer (1.5 molar, pH 8). The dye signal was evaluated after 30 minutes using a conventional spectrophotometer.

Screening for horseradish peroxidase inhibitory function was carried out by adding a sample (50 µl) of each culture supernatant to microtiter plate wells, followed by addition of horseradish peroxidase (0.2 nmolar) and gelatin (0.8%) in phosphate buffered saline solution, and the resulting mixtures were allowed to incubate for 10 minutes at room temperature.

Residual horseradish peroxidase activity was determined by adding a solution (100 µl) of o-phenylenediamine (1 mg/ml) in citrate/phosphate buffer (50 µl, 50 mmolar, pH 5.5), and measuring the amount of dye signal at 450 nm using a conventional spectrophotometer (100 mOD/minute).

The resulting antibody 6–89.1 was measured to diminish enzyme activity by only 6%.

The monoclonal binder antibody identified above as "B5-10" was prepared in a similar fashion. The particular binder antibody used in the following examples is not critical to the invention. Any suitable binder antibody as described above can be similarly used.

The binder antibodies were stored at 4° C. as separate stock solutions prior to use in assays, containing about 1 mg of antibody per ml of phosphate buffered saline solution and 0.02% merthiolate preservative.

Preparation of Conjugate of Diphenylhydantoin and Horseradish Peroxidase:

A water-soluble conjugate of a diphenylhydantoin hapten and amine-enriched horseradish peroxidase was prepared as follows. This preparation is representative only, and is not essential to preparing conjugates useful in the present invention. Alternative preparatory methods also exist.

The hapten, 5,5-diphenyl-3-{4-[4-(3-succinimidoxycarbonylpropionyl)-1-piperazinylcarbonyl]-butyl}-2,4-imidazolidinedione, was prepared by procedures described in EP-A-0 517 327 (published May 5, 1993). It is identified as "HD-2" in that publication. Amine-enriched horseradish peroxidase was prepared using the general procedure of Example 1 of U.S. Pat. No. 5,162,219, incorporated herein by reference.

The hapten was conjugated to amine-enriched horseradish peroxidase by dissolving "HD-2" (15.5 mg) in dry N,N-dimethylformamide (1.031 ml) containing 4'-hydroxyacetanilide (10 mmolar). A solution of amine-enriched horseradish peroxidase (1 ml, 10 mg/ml) in N-(2-hydroxyethyl)piperazine-N'-(3-propanesulfonic acid) buffer (pH 8, 0.1 molar) was combined with N,N'-dimethylformamide (500 µl) containing 4'-hydroxyacetanilide (10 mmolar) with vortex mixing and was then placed in a 42° C. water bath. The "HD-2" solution (500 µl) was added dropwise to the enzyme solution with vortex mixing so that the molar ratio was 50:1. The reaction mixture was incubated for 1 hour at 42° C. with gentle agitation.

The reaction product was dialyzed as follows:

a) Against a mixture of N,N'-dimethylformamide (1 liter) containing 4'-hydroxyacetanilide (10 mmolar) and the buffer noted above (pH 8, 0.1 molar) at a 1:1 ratio at 42° C. for 1 hour.

b) Dialysis condition a) was repeated.

c) Against the noted buffer (1.5 liters, 0.1 molar, pH 8) containing bovine serum albumin (0.1%) at 8° C. for 1.5 hours.

d) Against the noted buffer (1.5 liters, 0.1 molar, pH 8) at 8° C. for 18 hours.

e) Against tris(hydroxymethyl)aminomethane hydrochloride buffer (1.5 liters, 0.04 molar, pH 7.5) containing sodium chloride (0.15 molar) at 8° C. for 2 hours.

f) Dialysis condition e) was repeated for 4 hours.

The product solution contained 1.48 mg/ml of diphenylhydantoin-horseradish peroxidase conjugate, as determined by spectrophotometry.

Preparation of Conjugate of $PGE_2$ and Horseradish Peroxidase:

A water-soluble conjugate of $PGE_2$ and horseradish peroxidase was prepared by the following procedure. This procedure, however, is representative, because other useful procedures are also known.

A solution (0.5 ml) of $PGE_2$ (5 mg) in aqueous N,N'-dimethylformamide/dimethyl sulfoxide (13% and 26%, respectively) was treated with an equimolar amount of tributylamine (2.63 µl), cooled in an ice bath, and then mixed with an equimolar amount of isobutyl chloroformate (1.94 µl of a 1:100 solution in N,N-dimethylformamide). The resulting mixture was stirred in an ice bath for 20 minutes.

Amine-enriched horseradish peroxidase was prepared using the procedure of Example 1 of U.S. Pat. No. 5,162,219 (noted above), except that it was prepared on a larger scale, L-lysine was substituted for ethylenediamine, and 1-ethyl-3-(3-dimethylaminopropyl)carbodiimide hydrochloride was substituted for 1-(4-morpholinocarbonyl)-4-(2-sulfoethyl)pyridinium hydroxide, inner salt. A portion of the resulting solution of enriched enzyme (19.33 mg/ml) was diluted with 3-(N-morpholino)propanesulfonic acid buffer (0.02 molar) to 1 mg/ml. The pH was raised to 9 with sodium hydroxide (0.05 molar), then treated dropwise with the previously prepared $PGE_2$ solution (1.493 ml). The mixture was stirred for 90 minutes at room temperature, and the pH lowered to 7 with dilute hydrochloric acid. Ammonium hydroxide (0.578 ml, 0.2 molar, pH 7) was added to a final concentration of 0.02 molar, and the resulting mixture was incubated at room temperature for 2 hours. The resulting conjugate solution was desalted in gel filtration columns, concentrated and dialyzed first against water, then against phosphate buffered saline solution. The product solution contained 1.3 mg/ml (58% yield) of $PGE_2$-horseradish peroxidase conjugate, as determined by spectrophotometry.

The diphenylhydantoin-horseradish peroxidase conjugate ($3.29 \times 10^{-10}$ molar) and $PGE_2$-horseradish peroxidase conjugate ($1 \times 10^{-9}$ molar) described above were separately stored in 3-(N-morpholino)propanesulfonic acid buffer (0.2 molar, pH 7) containing bovine serum albumin (1%) and merthiolate (0.02%).

Monoclonal antibodies specific to diphenylhydantoin and monoclonal and polyclonal antibodies specific to $PGE_2$ used in the assays of the examples were either obtained from commercial sources or prepared using conventional procedures. These antibodies were separately immobilized as follows on particles of poly[styrene-co-p-(2-chloroethylsulfonylmethyl)styrene] (monomer weight ratio of 92:8, 1 µm average size). The monoclonal binder antibodies B5-10 were similarly immobilized.

A suspension (3% solids) of particles was mixed with the respective antibodies (0.829 mg/ml) for 24 hours at room temperature in borate buffer (0.1 molar, pH 8.5). The resulting attached coverage was about 0.025 g of antibodies per gram of particles for anti-$PGE_2$ antibodies, 0.025 g/g for anti-diphenylhydantoin antibodies, and 0.013 g/g for anti-horseradish peroxidase antibodies. The resulting immobilized antibodies, used as immobilized first or second receptors, were washed and resuspended in N-tris(hydroxymethyl)methyl-2-aminoethanesulfonic acid buffer (0.1 molar, pH 7) for use in assays.

Horseradish peroxidase, containing isoenzyme C, was obtained from Servac, Inc. (South Africa).

Enzyme substrate solution was prepared by adding a solution (5 ml) of 4,5-bis(4-dimethylaminophenyl)-2-(4-hydroxy-3-methoxyphenyl)imidazole leuco dye (1 g) in N,N-dimethylformamide to a solution (500 ml) of polyvinylpyrrolidone (125 g) and stirred for an hour. Diethylenetriamidepentaacetic acid (1 ml, 0.1 molar) was added to a solution (9500 ml) of monobasic sodium phosphate monohydrate (13.8 g) with stirring, followed by addition of 3'-chloro-4'-hydroxyacetanilide (9.4 g). The resulting mixture was stirred to dissolve the components, and the pH was adjusted to 6.8 with 50% sodium hydroxide. With vigorous stirring, it was then mixed with the leuco dye solution. Hydrogen peroxide (10 ml, 30%) was added, and the final mixture was stirred another 15 minutes.

A dye signal stop solution contained benzohydroxamic acid (0.1%) and merthiolate (0.01%) in phosphate buffered saline (0.05 molar, pH 7.3).

A wash solution contained TERGITOL™ 4 anionic surfactant (1.35%), casein (0.5%) and merthiolate (0.01%) in glycine buffer (pH 10).

Solutions of target diphenylhydantoin or $PGE_2$ were prepared in 3-(N-morpholino)propanesulfonic acid buffer (0.2 molar, pH 7) containing bovine serum albumin (1%).

In the embodiment of this invention wherein an immobilized first receptor is used (Examples 1 and 2), step A) and subsequent separation were carried out using an extraction device containing a tube (6 ml volume) to which was fitted a filter cap which contains a LOPRODYNE™ microporous membrane (1.2 µm average pore size, as described in U.S. Pat. No. 4,948,561 (noted above). In the embodiment where the first receptor is water-soluble, step A) was carried in a test tube.

Later steps of the present invention were carried out in a disposable test device from an EVALUSITE™ test kit [like those described in U.S. Pat. No. 5,132,085 (Pelanek)], containing three test wells, each having a LOPRODYNE™ microporous membrane (1.2 μm average pore size). Onto the membrane of each well was applied and dried, a suspension (1.8 μl, 0.3% solids) of the immobilized second receptor described above.

EXAMPLE 1

Assay for Prostaglandin $PGE_2$

The ligand $PGE_2$ was determined according to the method of the present invention as follows.

To a microcentrifuge tube was added, in order:

N-[tris(hydroxymethyl)methyl]-2-aminoethanesulfonic acid buffer (0.107 ml, 0.1 molar, pH 7), immobilized anti-$PGE_2$ antibody reagent (0.028 ml, 0.6% solids, final concentration), and unlabelled $PGE_2$ solution (0.03 ml, various ligand concentrations), followed by incubation for 30 minutes at room temperature. Water-soluble $PGE_2$-horseradish peroxidase conjugate (0.03 ml) was then added, followed by incubation for 5 minutes at room temperature. The contents were centrifuged in the tube for 8 minutes.

Supernatant from the tube was decanted into the test walls of the disposable test device containing immobilized anti-horseradish peroxidase antibodies. Where sufficient target $PGE_2$ was present in the test solution, the supernatant contained unbound water-soluble conjugate of $PGE_2$ and horseradish peroxidase.

After incubation for 5 minutes at room temperature, the wash solution (about 350 μl) was added to the test wells, drained and followed by a second wash. Three drops of the enzyme substrate solution were added. After incubation for 2 minutes at room temperature, the dye signal stop solution (3 drops) was added, and the resulting dye signal was evaluated.

Positive control assays were similarly carried out in the absence of target $PGE_2$ and immobilized anti-$PGE_2$ antibodies in the microcentrifuge tube. In such situation, all of the water-soluble conjugate was free to complex with the immobilized second receptor (antibodies) in the test device, providing the maximum dye signal.

Negative control assays were similarly carried out in the absence of target $PGE_2$, but with immobilized anti-$PGE_2$ antibodies present in the microcentrifuge tube. The resulting dye signal was from background only.

Figure 1:
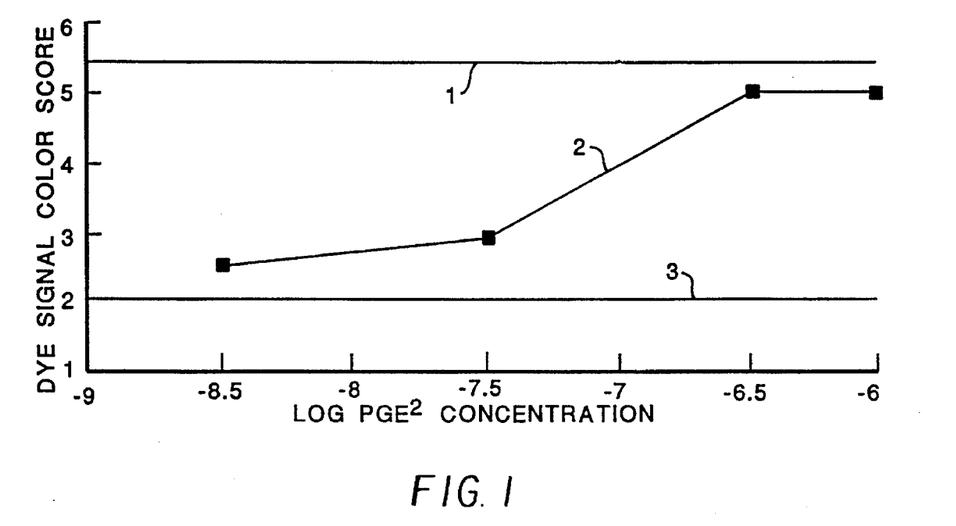
FIG. 1 is a graphical plot of dye signal color score versus log $PGE_2$ concentration and is described in more detail in Example 1 below.
Figure 2:
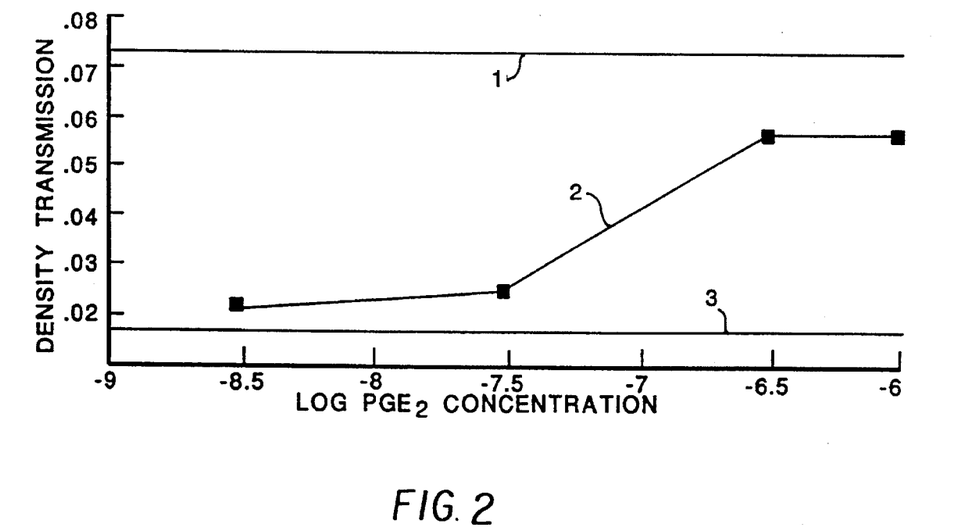
FIG. 2 is a graphical plot of dye signal density transmission versus log $PGE_2$ concentration and is described in more detail in Example 1 below.

A titration of dye signal above background was observed as a function of $PGE_2$ concentration with a detection limit between $1\times10^{-9}$ and $3\times10^{-9}$ molar $PGE_2$. FIGS. 1 and 2 show the results of these assays in the form of dose response curves, including the positive and negative controls (curves 1 and 3, respectively), and the assay of the invention (curve 2). In FIG. 1, dye signal (observed color score from a color density chart) is plotted on the y-axis and $PGE_2$ concentration [log($PGE_2$)] is plotted on the x-axis. FIG. 2 is a similar plot but with dye signal (density transmission) plotted on the y-axis. This assay demonstrates the sensitive detection of $PGE_2$, which is a marker for certain periodontal diseases.

EXAMPLE 2

Assay for Diphenylhydantoin

The ligand diphenylhydantoin (phenytoin) was determined according to the method of the present invention as follows.

To an extraction device was added, in order:

N-[tris(hydroxymethyl)methyl]-2-aminoethanesulfonic acid buffer (0.211 ml, 0.1 molar, pH 7), immobilized anti-diphenylhydantoin antibody reagent (0.059 ml, 0.2% solids, final concentration), and unlabelled diphenylhydantoin solution (0.03 ml, various ligand concentrations), followed by incubation for 5 minutes at room temperature. Water-soluble diphenylhydantoin-horseradish peroxidase conjugate (0.03 ml) was then added, followed by incubation for 5 minutes at room temperature. The filter cap was then placed on the tube.

Supernatant from the extraction tube was squeezed through the filter cap and applied to the test wells of the disposable test device containing the immobilized anti-diphenylhydantoin antibodies as the second receptor. Where sufficient target diphenylhydantoin was present, the supernatant contained unbound water-soluble conjugate of diphenylhydantoin and horseradish peroxidase.

After incubation for 5 minutes at room temperature, the wash solution (350 μl) was added to the test wells, drained and followed by a second wash. Three drops of the enzyme substrate solution were added. After incubation for 2 minutes at room temperature, the dye signal stop solution (3 drops) was added, and the resulting dye signal was evaluated.

Positive and negative control assays were similarly carried out as described in Example 1.

Figure 3:
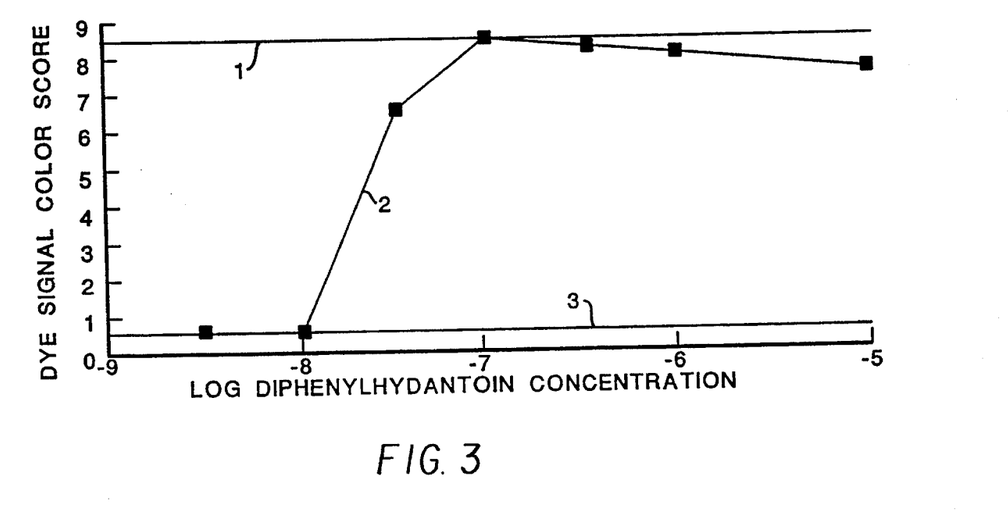
FIG. 3 is a graphical plot of dye signal color score versus log diphenylhydantoin concentration and is described in more detail in Example 2 below.
Figure 4:
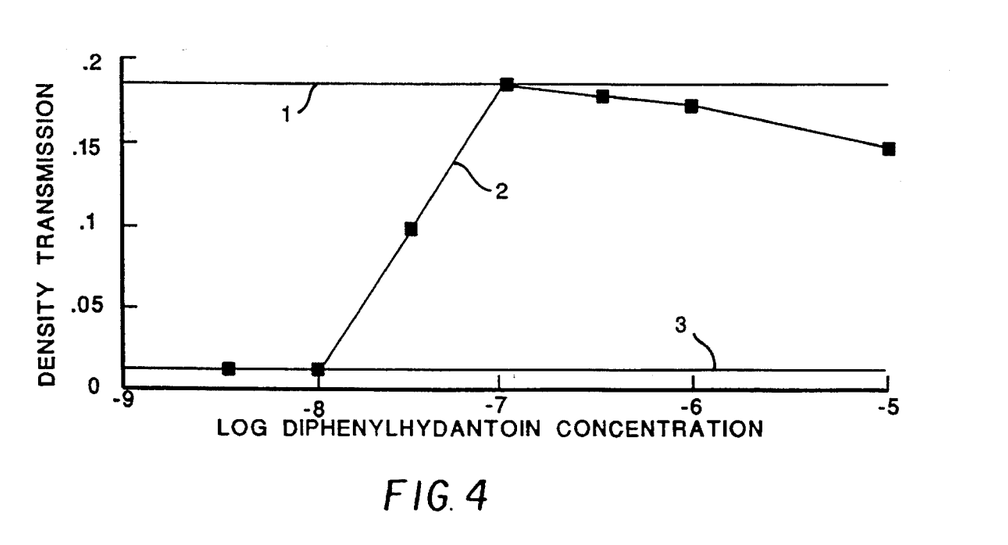
FIG. 4 is a graphical plot of dye signal density transmission versus log diphenylhydantoin concentration and is described in more detail in Example 2 below.

A titration of dye signal above background was observed as a function of diphenylhydantoin concentration with a detection limit of between $1\times10^{-8}$ and $3\times10^{-8}$ molar diphenylhydantoin. FIGS. 3 and 4 show the results of these assays in the form of dose response curves, including the positive and negative controls (curves 1 and 3, respectively), and the assay of the invention (curve 2). In FIG. 3, dye signal (observed color score from a color density chart) is plotted on the y-axis and diphenylhydantoin concentration [log(diphenylhydantoin)] is plotted on the x-axis. FIG. 4 is a similar plot with dye signal (density transmission) plotted on the y-axis.

EXAMPLE 3

Alternative Assay for Prostaglandin $PGE_2$

The ligand $PGE_2$ was determined according to an alternative embodiment of the present invention using a water-soluble (non-immobilized) first receptor as follows:

To a test tube was added, in order:

Anti-$PGE_2$ antibody (0.270 ml, 0.00316 mg/ml) in N-[tris(hydroxymethyl)methyl]-2-aminoethanesulfonic acid buffer (0.1 molar, pH 7), and unlabelled $PGE_2$ solution (0.03 ml, various ligand concentrations as in Example 1), followed by incubation for 5 minutes at room temperature. Water-soluble $PGE_2$-horseradish peroxidase conjugate (0.03 ml) was then added, followed by incubation for 5 minutes at room temperature.

The contents were decanted into the test wells of the disposable test device containing immobilized monoclonal anti-$PGE_2$ antibodies. Where sufficient target $PGE_2$ was present in the test solution, the supernatant contained unbound water-soluble conjugate of $PGE_2$ and horseradish peroxidase.

After incubation for 5 minutes at room temperature, the wash solution (about 350 μl) was added to the test wells, drained and followed by a second wash. Three drops of the enzyme substrate solution were added. After incubation for 2 minutes at room temperature, the dye signal stop solution (3 drops) was added, and the resulting dye signal was evaluated.

Positive control assays were similarly carried out in the absence of target $PGE_2$ and anti-$PGE_2$ antibodies in a test tube. In such situations, all of the water-soluble conjugate was free to complex with the immobilized second receptor (antibodies) in the test device, providing the maximum dye signal.

Negative control assays were similarly carried out in the absence of target $PGE_2$, but with anti-$PGE_2$ antibodies present in the test tube. The resulting dye signal was from background only.

A titration of dye signal above background was observed as a function of $PGE_2$ concentration with a detection limit between $1\times10^{-8}$ and $3\times10^{-8}$ molar $PGE_2$. This assay demonstrates a detection of $PGE_2$, which is a marker for certain periodontal diseases.

The invention has been described in detail with particular reference to preferred embodiments thereof, but it will be understood that variations and modifications can be effected within the spirit and scope of the invention.

We claim:

1. A specific binding method for the detection of a target specific binding ligand comprising the steps of:
   A) bringing together, in any order:
      1) a fluid sample suspected of containing a target specific binding ligand,
      2) an immobilized first receptor for said target specific binding ligand, and
      3) a water-soluble conjugate of said target specific binding ligand and a reporter enzyme,
   to form a mixture containing a water-insoluble complex between said first receptor and said conjugate,
   B) separating said water-insoluble complex of said first receptor from any uncomplexed water soluble conjugate,
   C) bringing together a sample of said uncomplexed water-soluble conjugate, and an immobilized second receptor, wherein said second receptor is specific for said reporter enzyme, and further wherein said second receptor inhibits the activity of said reporter enzyme by less than 20%,
   to form a water-insoluble reaction product of said immobilized second receptor and any uncomplexed water-soluble conjugate,
   D) separating said water insoluble reaction product formed in step C) from any unreacted water-soluble conjugate, and
   E) detecting any signal generated from said separated water-insoluble reaction product as a determination of said target specific binding ligand in said fluid sample.

2. The method of claim 1 wherein said reporter enzyme is a peroxidase, alkaline phosphatase, creative kinase, glucose oxidase, urease, β-galactosidase or glucose-6-phosphate dehydrogenase.

3. The method of claim 2 wherein said reporter enzyme is horseradish peroxidase.

4. The method of claim 1 wherein said detection step E) is carried out by evaluating a colorimetric signal generated from said reporter enzyme in the presence of a suitable substrate.

5. The method of claim 1 for the detection of a low molecular weight target specific binding ligand having a molecular mass of less than 500 daltons, wherein said first receptor is an immobilized antibody specific to said low molecular weight target specific binding ligand, and said immobilized second receptor is an antibody specific to said reporter enzyme.

6. The method of claim 5 for the detection of prostaglandin $E_2$ ($PGE_2$) wherein said reporter enzyme is horseradish peroxidase, said immobilized first receptor is an antibody specific to $PGE_2$, and said immobilized second receptor is an antibody specific to horseradish peroxidase.

7. The method of claim 1 wherein said first and second receptors are immobilized on polymeric particles.

8. The method of claim 1 wherein:
   said fluid sample and said immobilized first receptor are brought together prior to contact with said water-soluble conjugate,
   said water-insoluble complex formed in step A) is separated from said uncomplexed water-insoluble conjugate in said supernatant by filtration, and
   said immobilized second receptor is disposed on a filtration membrane through which said supernatant is drained in step D).

9. A test kit useful for the detection of a target specific binding ligand comprising in individual packaging:
   a water-soluble conjugate of a target specific binding ligand and a reporter enzyme,
   an immobilized first receptor for said target specific binding ligand,
   an immobilized second receptor, wherein said second receptor is specific for said reporter enzyme, and further wherein said second receptor inhibits the activity of said reporter enzyme by less than 20%.

10. The test kit of claim 9 further comprising at least one of the following, in individual packaging:
    one or more reagents for providing a colorimetric, fluorometric or chemiluminescent signal in response to said reporter enzyme,
    a wash solution,
    a disposable test device, or
    a filtration device.

11. The test kit of claim 9 wherein said first and second receptors are immobilized on polymeric particles.

12. The test kit of claim 11 wherein said reporter enzyme is a peroxidase, and said second receptor is an antibody to a peroxidase.

13. The test kit of claim 9 wherein said first receptor is antibodies to $PGE_2$, and said reporter enzyme is horseradish peroxidase.

14. The test kit of claim 9 further comprising a disposable test device having therein a microporous filtration membrane on which are disposed polymeric particles to which said second receptor is affixed, said second receptor being antibodies specific to said reporter enzyme.

* * * * *

UNITED STATES PATENT AND TRADEMARK OFFICE
CERTIFICATE OF CORRECTION

PATENT NO. : 5,589,344
DATED      : Dec. 31, 1996
INVENTOR(S) : Paul B. Contestable; Brian A. Snyder It is certified that error appears in the above-indentified patent and that said Letters Patent is hereby corrected as shown below:

Column 17, line 55: delete "creative" and insert therefor --creatine--.

Signed and Sealed this

Twenty-third Day of September, 1997

Attest:

BRUCE LEHMAN

Attesting Officer

Commissioner of Patents and Trademarks